(12) United States Patent
Yoon et al.

(10) Patent No.: US 10,696,989 B2
(45) Date of Patent: Jun. 30, 2020

(54) BIOLOGICAL METHOD FOR PREPARING HEME IRON NOT DERIVED FROM PORCINE BLOOD

(71) Applicant: INTRON BIOTECHNOLOGY, INC., Gyeonggi-do (KR)

(72) Inventors: Seong Jun Yoon, Seoul (KR); Jung In Pyo, Seoul (KR); Soon Hye Hwang, Gyeonggi-do (KR); Soo Youn Jun, Seoul (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 16/475,409

(22) PCT Filed: Dec. 6, 2017

(86) PCT No.: PCT/KR2017/014173
§ 371 (c)(1),
(2) Date: Jul. 2, 2019

(87) PCT Pub. No.: WO2018/128280
PCT Pub. Date: Jul. 12, 2018

(65) Prior Publication Data
US 2019/0352680 A1 Nov. 21, 2019

(30) Foreign Application Priority Data
Jan. 3, 2017 (KR) .................. 10-2017-0000516

(51) Int. Cl.
*C12P 9/00* (2006.01)
*C07D 487/22* (2006.01)
(52) U.S. Cl.
CPC ............... *C12P 9/00* (2013.01); *C07D 487/22* (2013.01)
(58) Field of Classification Search
CPC ........................................................ C12P 9/00
See application file for complete search history.

(56) References Cited

U.S. PATENT DOCUMENTS

| 4,431,581 A | 2/1984 | Lindroos |
| 5,008,388 A | 4/1991 | Inberg et al. |
| 9,334,513 B2 | 5/2016 | Kim |
| 2008/0242857 A1 | 10/2008 | Martin et al. |
| 2011/0213142 A1 | 9/2011 | Kim |

FOREIGN PATENT DOCUMENTS

| KR | 1020120077726 A | 7/2012 |
| KR | 1020110070977 A | 5/2016 |
| WO | PCT/KR2017/014173 | 12/2017 |
| WO | WO 2018/128280 A1 | 7/2018 |

OTHER PUBLICATIONS

Da Silva, R. R. et al., "Luminol in the Forensic Science", Journal of Biotechnology and Biodiversity, 2012, vol. 3, No. 4, pp. 172-177.
Kwon, O.H et al., "Potential Application of the Recombinant *Escherichia coli*-synthesized Heme as a Bioavailable Iron Source", Journal of Microbiology and Biotechnology, 2009, vol. 19, No. 6, pp. 604-609.
Lee, M. J. et al., "Porphyrin Derivatives from a Recombinant *Escherichia coli* Grown on Chemically Defined Medium", Journal of Microbiology and Biotechnology, 2012, vol. 22, No. 12, pp. 1653-1658.
Liu, et. al.,"Physicochemical Properties of Aggregates of Globin Hydrolysates" J. Agric. Food Chem.1996,44(10):2957-2961.
International Search Report dated Mar. 13, 2018 by the International Searching Authority for International Application No. PCT/KR2017/014173, filed on Dec. 6, 2017 and published as WO 2018/128280 on Jul. 12, 2018 (Applicant—Intron Biotechnology, Inc. ) (Translation—3 Pages).

*Primary Examiner* — Joseph R Kosack
(74) *Attorney, Agent, or Firm* — Ballard Spahr LLP

(57) ABSTRACT

The present invention relates to heme iron not derived from porcine blood and a method of preparing the same, and more particularly to a method of biologically preparing heme iron not derived from porcine blood, a method of preparing a salt thereof, and an iron supplement containing the salt thus prepared as an active ingredient.

5 Claims, 3 Drawing Sheets

[FIG. 1]
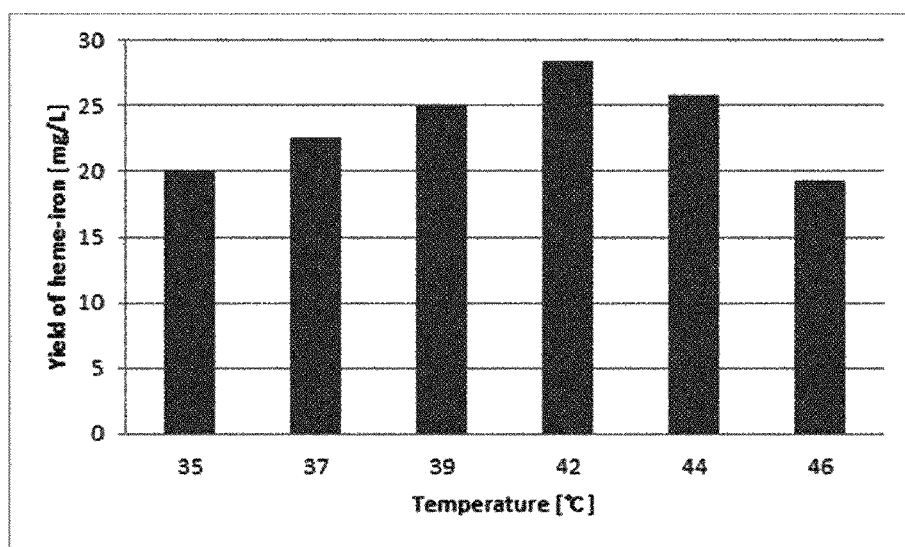

[FIG. 2]
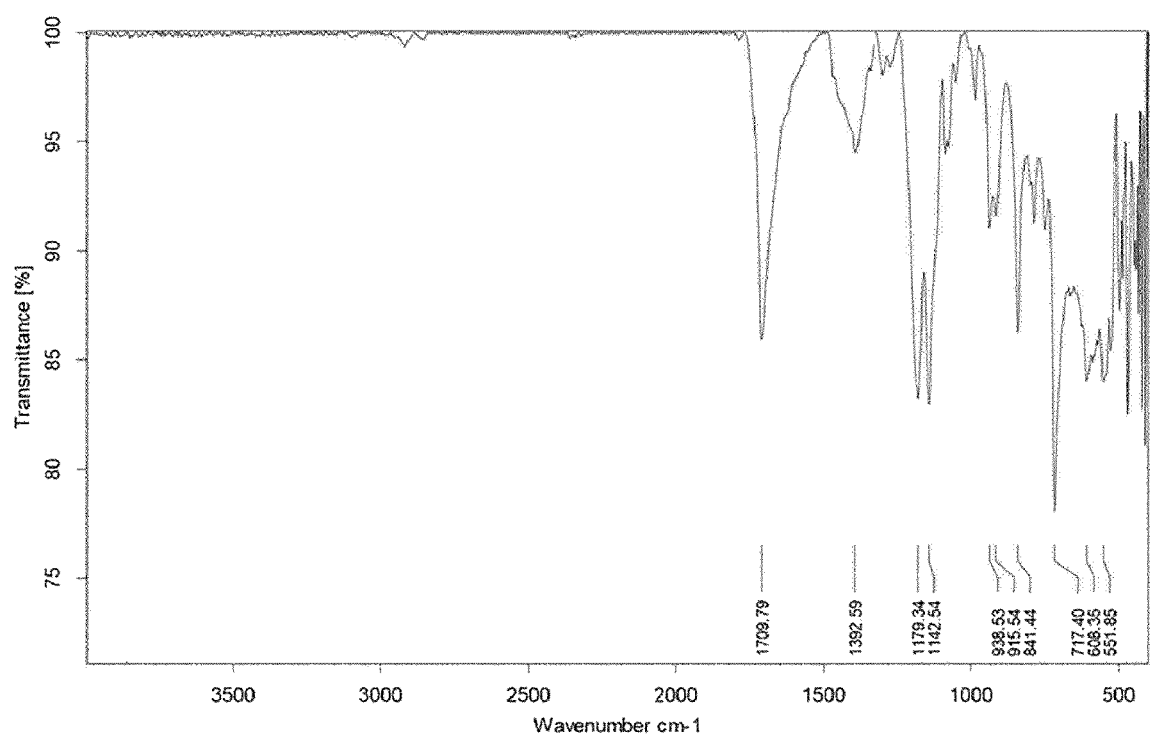

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM
RECEIPT FOR ORIGINAL DEPOSIT
issued pursuant to Rule 7.1

NAME OF DEPOSITOR: Intron Biotechnology
ADDRESS: Intron Biotechnology, 137 Sagimakgol-ro, Joongwon-gu, Seongnam, Kyeonggi-do, Republic of Korea (13202)

| I. IDENTIFICATION OF THE MICROORGANISM | |
|---|---|
| Identification reference given by the DEPOSITOR:<br>*Escherichia coli* DH5α pLEX_HMD | Accession number given by the INTERNATIONAL DEPOSITARY AUTHORITY:<br>KCTC 13173BP |
| II. SCIENTIFIC DESCRIPTION AND PROPOSED TAXONOMIC DESIGNATION | |
| The microorganism identified under I above was accompanied by:<br>[ ] a scientific description<br>[ ] a proposed taxonomic designation | |
| III. RECEIPT AND ACCEPTANCE | |
| This International Depositary Authority accepts the microorganism identified under I above, which was received thereby on December 21, 2016 | |
| V. INTERNATIONAL DEPOSITARY AUTHORITY | |
| Name: Korean Collection for Type Cultures<br><br>Address: Biological Resource Center in Korea Research Institute of Bioscience and Biotechnology (KRIBB)    181 Ypsin-gil, Jeongup, Jeollabuk-do, Republic of Korea (56212) | Signature(s) of person(s) having power to represent the International Depositary Authority or of authorized official(s):<br><br>Representative<br>December 28, 2016 |

[Fig. 3]

BIOLOGICAL METHOD FOR PREPARING HEME IRON NOT DERIVED FROM PORCINE BLOOD

CROSS-REFERENCE TO RELATED APPLICATIONS

This application is a U.S. National Phase Application of International Application No. PCT/KR2017/014173, filed Dec. 6, 2017, which claims priority to Korean Application No. 10-2017-0000516, filed Jan. 3, 2017, each of which are hereby incorporated by reference in their entirety.

TECHNICAL FIELD

The present invention relates to heme iron containing no animal-derived component and a method of preparing the same, and more particularly to a method of biologically preparing heme iron not derived from porcine blood, which is characterized in containing no animal-derived component, a method of preparing a salt thereof, and an iron supplement containing the salt thus prepared as an active ingredient.

BACKGROUND ART

Iron (Fe) is a trace element that plays an essential role for oxygen transport in the body, and is an important constituent of hemoglobin, myoglobin, cytochrome, iron/sulfur protein and biomolecular structures. The total amount of iron in the body is about 3 to 4 g, 60 to 65% of which is bound to hemoglobin in circulating erythrocytes, and the remaining 30 to 35% is present as storage iron (ferritin). Iron is also present in the form of tissue iron and serum iron (transferrin), and furthermore, there is a small amount of iron in myoglobin of the muscles.

Iron is not synthesized in the body and thus must be acquired entirely through intake, and exists in two types, heme iron and nonheme iron. Heme iron is an iron complex having a moiety having the same structure as the heme of hemoglobin in the body, and nonheme iron is an iron complex not having a moiety having the same structure as the heme of hemoglobin. These two types of iron may be used as iron supplements (iron supplementary compound), and the bioavailability of heme iron is known to be much higher than that of nonheme iron. Also, the absorption of heme iron in the body is not affected by other dietary factors. Moreover, heme iron has the advantage of not causing various side effects (constipation, gastrointestinal disorders, etc.) that have been reported for nonheme iron.

Generally, heme iron is manufactured from blood of slaughtered animal, such as porcine blood. The heme iron is prepared from slaughterhouse blood by a manner in which hemoglobin is first separated from the slaughterhouse blood and then heme iron is isolated from the separated hemoglobin. The separation of heme iron from hemoglobin may be performed through a method of using an alcohol and an imidazole derivative (Lindroos, U.S. Pat. No. 4,431,581), a method of adding amino acids thereto (Ingberg, et. al., U.S. Pat. No. 5,008,388), a method of performing decomposition at a high temperature using a highly concentrated organic acid (Liu, et. al., *J. Agric.* Food Chem., 44, 2957, 1996), a method of using a protease, and the like.

Heme iron thus prepared has many problems that are not present in nonheme iron, such as the risk of infection by animal-derived infection sources, livestock growth hormone contamination, and residual antibiotics. Moreover, the preparation of heme iron as described above involves the production of heme iron from blood obtained from the slaughter of animals such as pigs, which is forbidden by Islam, and thus the heme iron above prepared does not conform to halal regulations, undesirably obstructing the use thereof as an iron supplement by Muslims.

Therefore, it is necessary to develop a method of preparing heme iron not derived from porcine blood.

DISCLOSURE

Technical Problem

Accordingly, the present invention has been made keeping in mind the problems encountered in the related art and is intended to solve such problems.

An objective of the present invention is to provide a process of biologically preparing heme iron that is not derived from porcine blood.

Another objective of the present invention is to provide a heme iron production strain, namely *Escherichia coli* DH5α pLEX_HMD (Accession number: KCTC 13173BP), which may be used in the process of biologically preparing heme iron not derived from porcine blood.

Still another objective of the present invention is to provide a method of preparing a salt of the heme iron obtained through the process of biologically preparing heme iron not derived from porcine blood.

Yet another objective of the present invention is to provide a pharmaceutical composition for the prevention of iron-deficiency anemia, containing the salt of the heme iron obtained through the process of biologically preparing heme iron not derived from porcine blood, as a main ingredient, without containing any animal component.

Still yet another objective of the present invention is to provide a pharmaceutical composition for the treatment of iron-deficiency anemia, containing the salt of the heme iron obtained through the process of biologically preparing heme iron not derived from porcine blood, as a main ingredient, without containing any animal component.

Technical Solution

In order to accomplish the above objectives, the present inventors have, as the result of intensive study, developed a process of biologically preparing heme iron not derived from porcine blood, a method of preparing a salt of the heme iron above prepared, and a pharmaceutical composition containing no animal component using the salt of the heme iron above prepared, and have ascertained that the composition may be effectively utilized for the treatment of iron-deficiency anemia, thus culminating in the present invention.

In the process of biologically preparing heme iron not derived from porcine blood, *Escherichia coli* DH5α pLEX_HMD (Accession number: KCTC 13173BP) is used as a production strain. *Escherichia coli* DH5α pLEX_HMD was deposited at the Korean Collection for Type Cultures in the Korea Research Institute of Bioscience and Biotechnology on Dec. 21, 2016 (Accession number: KCTC 13173BP).

In the process of biologically preparing heme iron not derived from porcine blood, a higher culture temperature is adopted than the culture temperature that is applied in a typical process of culturing *Escherichia coli*. The culture temperature suitable for the present invention is preferably 39 to 44° C., more preferably 41 to 43° C., and most preferably 42° C. The application of such a slightly high culture temperature enables the maximum production of heme iron using the production strain of the present invention.

In the process of biologically preparing heme iron not derived from porcine blood, a medium containing no animal-derived component is used. To this end, in the present invention, medium components include plant-derived peptone and a yeast extract prepared from yeast cultured in a plant-derived medium.

In the process of biologically preparing heme iron not derived from porcine blood, the pH of the culture process is maintained in the range of 7 to 9, and preferably in the range of 8 to 9. Here, the pH is adjusted using succinic acid. When succinic acid is used to adjust the pH in this process, succinic acid is a substance used as a substrate in the biosynthesis of heme iron, which is advantageous for the high efficient production of heme iron.

In the process of biologically preparing heme iron not derived from porcine blood, extraction of produced heme iron from cultured cells may be performed through a primary extraction process and a secondary extraction process. In the present invention, the primary extraction process is characterized by conduction through celite filtration using an organic solvent, thereby facilitating the recovery of heme iron and increasing the yield of heme iron. Also, the secondary extraction process is conducted through solvent extraction. Here, examples of the solvent may include ethyl acetate, butyl acetate, methylene chloride, 1,2-dichloroethane, chloroform, carbon tetrachloride, and methyl ethyl ketone, and the use of methylene chloride or chloroform is most preferable.

In the method of preparing the salt of the heme iron obtained through the process of biologically preparing heme iron not derived from porcine blood, the salt of heme iron above prepared is a material having the structure of Chemical Formula 1 below.

[Chemical Formula 1]

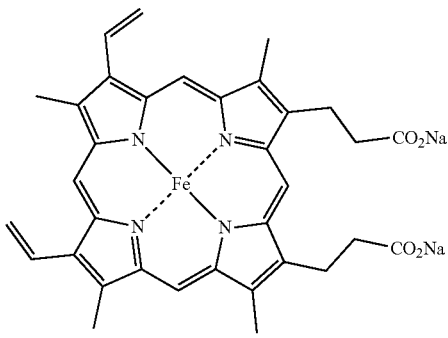

In the method of preparing the salt of the heme iron obtained through the process of biologically preparing heme iron not derived from porcine blood, the chlorination reaction for preparing the salt may be carried out at room temperature using a NaOH aqueous solution or a KOH aqueous solution. Here, the use of a NaOH aqueous solution is more preferable.

As used herein, the term "heme iron" refers to an iron complex comprising a moiety having the same structure as the heme of hemoglobin in the body, and the term "nonheme iron" refers to an iron complex not comprising a moiety having the same structure as the heme of hemoglobin.

A pharmaceutically acceptable carrier, which is contained in the composition of the present invention, may be any example thereof typically useful for formulation, and may include, but is not limited to, lactose, dextrose, sucrose, sorbitol, mannitol, starch, acacia rubber, calcium phosphate, alginate, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil and the like. The composition of the present invention may further contain, in addition to the above components, a lubricant, a wetting agent, a sweetener, a flavoring agent, an emulsifier, a suspending agent, a preservative, and the like.

The composition of the present invention may be formulated using a pharmaceutically acceptable carrier and/or excipient in accordance with a method that may be easily carried out by those skilled in the art to which the present invention belongs, and be prepared in a unit dosage form or insert the same into a multi-dose container. Here, the formulation thereof may be provided in the form of a solution in an oil or aqueous medium, a suspension or an emulsion, or in the form of an extract, a powder, a granule, a tablet, or a capsule, and may additionally contain a dispersant or a stabilizer.

Advantageous Effects

According to the present invention, a process of biologically preparing heme iron not derived from porcine blood can be provided. The heme iron thus prepared can provide various characteristic advantages of heme iron compared to nonheme iron, and can also overcome many problems related with existing heme iron made from porcine blood. In particular, since the use of porcine blood is fundamentally excluded, the heme iron thus prepared can also be utilized in the production of halal iron supplements. Moreover, the process of preparing heme iron according to the present invention is advantageous because it is based on a biological preparation process and thus the preparation process can be performed under mild conditions.

DESCRIPTION OF DRAWINGS

FIG. 1 shows the results under optimal culture temperature conditions; and

FIG. 2 shows the analysis results of FT-IR (Fourier transform infrared spectroscopy) for identification of prepared heme iron.

FIG. 3 shows the receipt of original deposit of *Escherichia coli* DH5α pLEX_HMD.

MODE FOR INVENTION

Hereinafter, a better understanding of the present invention will be given through the following examples, which are merely set forth to illustrate the present invention but are not to be construed as limiting the scope of the present invention.

Example 1: Preparation of Heme Iron Production Strain

With reference to the heme biosynthesis pathway in microorganisms in the present invention, a heme iron production strain was prepared through several trial-and-error steps. The heme iron production strain thus prepared was *Escherichia coli* DH5α pLEX_HMD, which is DH5α-based

*Escherichia coli* transformed with a plasmid designed for heme biosynthesis, particularly a plasmid containing a self-expression promoter $P_L$, an ALA synthase gene (HemA), a NADP-dependent malic enzyme gene (MaeB), and a dicarboxylic acid transport protein gene (DctA), and the strain thus prepared was deposited at the Korean Collection for Type Cultures in the Korea Research Institute of Bioscience and Biotechnology on Dec. 21, 2016 (Accession number: KCTC 13173BP).

Based on the comparing results of the heme iron production capability thereof with strains prepared using MG1655, Top10, BL21, and Rosetta gami, the production strain *Escherichia coli* DH5α pLEX_HMD exhibited superior heme iron production capability compared to the other *Escherichia coli* strains containing the same plasmid.

The heme iron production capability was compared as follows. 10 ml of a LB (Luria-Bertani) medium (10 g/L peptone, 5 g/L yeast extract, and 10 g/L NaCl) containing 50 μg/ml ampicillin was placed in a 50 ml conical tube, and each strain was seeded therein and then cultured overnight at 37° C. and 200 rpm using a rotary shaking incubator. Next, 1 ml of the culture broth obtained after overnight culture was seeded in each of five 250 ml Erlenmeyer flasks added with 50 ml of an S medium (10 g/L peptone, 5 g/L yeast extract, 5 g/L $KH_2PO_4$, 10 g/L succinate, 2 g/L glycine, and 10 mg/L $FeCl_2 \cdot 4H_2O$) containing 50 μg/ml ampicillin, and was then cultured at 37° C. and 200 rpm for 4 hr. After culturing for 4 hr, 2 ml of the culture broth was seeded in a 250 ml Erlenmeyer flask added with 100 ml of an S medium containing 50 μg/ml ampicillin, and was then cultured at 37° C. and 200 rpm for 48 hr, after which the resulting cells were recovered, based on which the extent of production of heme iron was compared. The results are shown below.

TABLE 1

Comparison of heme iron production capability

| | Production strain | Strain prepared from MG1655 | Strain prepared from Top10 | Strain prepared from BL21 | Strain prepared from Rosetta gami |
|---|---|---|---|---|---|
| Recovered cells [g/L] | 13.96 | 13.7 | 10.55 | 13 | 9 |
| Recovered heme iron [mg/L] | 6.1 | 2.8 | 4.1 | 4.3 | 3.3 |

As is apparent from the above results, the production strain *Escherichia coli* DH5α pLEX_HMD can be found to have superior heme iron production capability.

Example 2: Optimization of Heme Iron Production Conditions

Using the production strain *Escherichia coli* DH5α pLEX_HMD prepared in Example 1, optimization of the production process, including optimization of the medium composition, etc., was performed. FIG. 1 illustrates the results of optimization of the culture temperature as one of conditions for optimizing the production process. The production conditions of heme iron finally established through several processes for obtaining optimal production conditions are summarized below.

TABLE 2

Optimal heme iron production conditions

| Items | Optimal conditions |
|---|---|
| Seed culture medium composition | 10 g/L peptone, 5 g/L yeast extract, 10 g/L NaCl |
| Seed culture period | $1^{st}$ seed culture: overnight culture $2^{nd}$ seed culture: 4 hr |
| Main culture medium composition | 10 g/L peptone, 5 g/L yeast extract, 5 g/L $KH_2PO_4$, 10 g/L succinate, 2 g/L glycine and 10 mg/L $FeCl_2 \cdot 4H_2O$ |
| Culture temperature | Seed culture: 37° C. Main culture: 42° C. |
| Stirring rate | 200 rpm |
| pH | 8 to 9 (adjusted using succinic acid) |
| Production period (Main culture period) | 72 hr |

Example 3: Optimization of Heme Iron Purification Conditions

In the present Example, a heme iron purification process was developed, and specific conditions thereof were optimized. The finally established purification conditions of heme iron are as follows.

The culture broth of the heme iron production strain *Escherichia coli* DH5α pLEX_HMD was centrifuged at 3,000 g at 4° C. for 15 min, thus recovering cells thereof. The cells thus recovered were washed two times by suspending the same in PBS (Phosphate Buffered Saline) and then performing centrifugation. The finally recovered cells were naturally dried for about 30 min and then weighed. Typically, it was possible to recover 40 to 50 g of cells from 5 L of a culture broth. The recovered cells were added with cold acid-acetone and thus heme iron was extracted. Here, the cold acid-acetone that was used was prepared by mixing 998 ml of acetone at −20° C. with 2 ml of hydrochloric acid. The addition of the cold acid-acetone was conducted by a manner in which 1 L of cold acid-acetone was added to the cells recovered from 5 L of the culture broth. The extraction of heme iron using acid-acetone was performed at 4° C. for 5 days. The solution obtained through heme iron extraction for 5 days was passed through a celite-packed column to thus recover acetone containing heme iron. The acetone containing heme iron thus obtained was concentrated using a rotary evaporator. Here, concentration was performed until the volume was reduced from 1 L to 30 ml. The solution thus obtained was added with a 10-fold volume of methylene chloride, mixed thoroughly and then allowed to stand until layers were separated. After separation of the layers, the lower layer was recovered and concentrated using a rotary evaporator. Here, concentration was performed until the volume became 30 ml. A portion of the sample thus obtained was subjected to FT-IR (Fourier transform infrared spectroscopy). The analysis results thereof are shown in FIG. 2. After concentration, a NaOH aqueous solution was added in an amount of 2.1 equivalents based on the equivalents of heme iron contained in the concentrate, mixed thoroughly and then allowed to stand until layers were separated. After separation of the layers, the upper layer was recovered and freeze-dried, thereby yielding a salt of heme iron in a powder phase, as represented by Chemical Formula 1.

Example 4: Identification of Prepared Heme Iron

In order to identify the prepared heme iron and the salt thereof, various analyses were performed. Specifically, FT- IR, mass spectrometry, UV-vis spectrophotometry, and ICP-OES were conducted. The analysis results of heme iron are summarized below. These results were consistent with expectations. For reference, the results of FT-IR are shown in FIG. 2.

TABLE 3

Analysis results of heme iron

| Analysis method | Analysis results |
|---|---|
| FT-IR | 1709, 1392, 1179, 1142, 938, 915, 841, 717, 608, 551 cm$^{-1}$ |
| Mass spectrometry | (ESI) Calcd for $C_{34}H_{32}FeN_4O_4$: 616.2, found: m/z 616.2 |
| UV-vis spectrophotometry | (DMSO, nm) $\lambda_{max}$ 348, 386 |
| ICP-OES | Calcd for Fe: 9.06%, found: 9.0% |

Meanwhile, the analysis results for the salt of heme iron are summarized below. These results were consistent with expectations.

TABLE 4

Analysis results for salt of heme iron

| Analysis method | Analysis results |
|---|---|
| FT-IR | 1682, 1559, 1412, 1208, 1144, 880, 834, 726, 602, 541 cm$^{-1}$ |
| Mass spectrometry | (ESI) Calcd for $C_{34}H_{30}FeN_4Na_2O_4$: 660.1, found: m/z 660.2 |

Example 5: Evaluation for Effectiveness of Heme Iron as Iron Supplementary Source The salt of the heme iron prepared according to the present invention was dissolved in saline and administered to iron-deficiency-anemia-induced animals, whereby the effectiveness of the salt of the heme iron prepared according to the present invention on alleviating anemia was evaluated.

Specifically, thirty 7-week-old Sprague-Dawley rats (female) were divided into 3 groups of 10 rats per group, among which one group was fed with normal feed in an amount of 10% of body weight daily for one month (Group 1; control), and the remaining two groups were fed with iron-deficient feed in an amount of 10% of body weight daily for one month to induce iron-deficiency anemia (Group 2 and Group 3). After one month of feeding, it was confirmed that iron-deficiency anemia was induced in the individual rat belonging to Group 2 and Group 3. Then, one of the anemia-induced groups was orally administered once a day with saline alone (Group 2), and the other anemia-induced group was orally administered once a day with saline containing heme iron (0.1 mg Fe/500 μl saline) (Group 3). The administration continued for 30 days, and the occurrence of abnormal symptoms was monitored during the administration period. After 30 days of administration, blood was collected, and whether anemia was alleviated was evaluated. During 30 days of administration to Group 2 and Group 3, Group 1 was continuously fed with normal feed, and Group 2 and Group 3 were fed with iron-deficient feed. There were no abnormal symptoms in any animals during the 30 days of administration period. The analysis results of blood collection are shown below.

TABLE 5

Analysis results of blood collection

| Group No. | Treatment | Weight of rats on 30$^{th}$ day after administration [g] | Blood test | | | |
|---|---|---|---|---|---|---|
| | | | Hemoglobin content [g/dl] | RBC [×10$^6$/μl] | Mean corpuscular volume [fl] | Hematocrit [%] |
| Group 1 | Normal feed | 273.8 ± 3.3 | 14.6 ± 0.9 | 8.43 ± 0.2 | 49.5 ± 1.3 | 36.0 ± 2.2 |
| Group 2 | Iron-deficient feed + saline | 288.2 ± 1.4 | 11.9 ± 0.7 | 8.52 ± 0.1 | 39.3 ± 3.2 | 35.6 ± 1.5 |
| Group 3 | Iron-deficient feed + home iron | 265.2 ± 1.1 | 14.2 ± 0.4 | 8.59 ± 0.1 | 48.2 ± 2.2 | 35.8 ± 1.9 |

As is apparent from the above results, the heme iron of the present invention can be concluded to be effective at alleviating iron-deficiency anemia and is thus efficient material as an iron supplementary source. Also, the heme iron of the present invention and the salt thereof can be confirmed to be useful not only in the treatment of iron-deficiency anemia but also in the prevention thereof.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

[Accession Number]
Name of Depositary Authority: KCTC
Accession number: KCTC 13173BP
Accession date: 20161221

The invention claimed is:
1. A method of biologically preparing a salt of heme iron of Chemical Formula 1 below, not derived from porcine blood and containing no animal component, the method comprising:
A) producing heme iron by culturing *Escherichia coli* DH5α pLEX_HMD (Accession number: KCTC 13173BP) at 39 to 44° C. and a pH of 7 to 9 in a medium containing no animal component;
B) purifying the heme iron produced in step A); and
C) preparing a salt of the heme iron purified in step B)

[Chemical Formula 1]

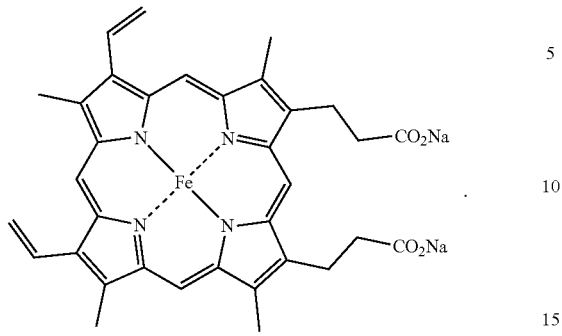

2. The method of claim 1, wherein the medium includes plant-derived peptone and a yeast extract prepared from yeast cultured in a plant-derived medium.

3. The method of claim 1, wherein the pH is adjusted using succinic acid.

4. The method of claim 1, wherein step B) is performed through filtration process using diatomaceous earth.

5. The method of claim 4, wherein the diatomaceous earth is Celite®545.

* * * * *